| United States Patent [19] | [11] | 4,057,576 |
|---|---|---|
| Bachmann et al. | [45] | Nov. 8, 1977 |

[54] PROCESS FOR ISOLATING 2-HYDROXYNAPHTHALENE CARBOXYLIC ACIDS FROM REACTION MIXTURES OF THE ALKALI METAL SALTS OF 2-HYDROXYNAPHTHALENE WITH CARBON DIOXIDE

[75] Inventors: Wilfried Bachmann, Frankfurt am Main; Christian Gnabs, Kelkheim, Taunus; Kurt Janecka, Offenbach (Main); Eberhard Mundlos, Heusenstamm; Theodor Papenfuhs, Frankfurt am Main; Gerhard Waese, Dietzenbach, all of Germany

[73] Assignee: Hoechst Aktiengesellschaft, Frankfurt am Main, Germany

[21] Appl. No.: 583,295

[22] Filed: June 3, 1975

[30] Foreign Application Priority Data

June 4, 1974 Germany .............................. 2426852

[51] Int. Cl.$^2$ ..................... C07C 51/44; C07C 51/48; C07C 37/28
[52] U.S. Cl. ............................. 260/525; 260/520 A; 260/621 A
[58] Field of Search ............... 260/520 R, 520 A, 525, 260/621 A, 619 A

[56] References Cited

U.S. PATENT DOCUMENTS

| 2,132,356 | 10/1938 | Lecher et al. .................... 260/520 A |
|---|---|---|
| 2,534,022 | 12/1950 | Higgins ............................ 260/520 A |
| 2,544,881 | 3/1951 | Hodges ............................ 260/520 A |
| 2,807,643 | 9/1957 | Hartley ............................ 260/520 A |
| 3,228,963 | 1/1966 | Joo et al. ......................... 260/520 R |
| 3,405,169 | 10/1968 | Levy et al. ....................... 260/520 A |
| 3,405,170 | 10/1968 | Levy et al. ....................... 260/520 A |
| 3,655,744 | 4/1972 | Yasuhara et al. ................ 260/520 A |

*Primary Examiner*—Norman Morgenstern
*Attorney, Agent, or Firm*—Connolly and Hutz

[57] ABSTRACT

An improved process for isolating 2-hydroxynaphthalenecarboxylic acids from reaction mixtures of the alkali metal salts of the 2-hydroxynaphthalene with carbon dioxide had been found which comprises diluting with water the reaction mixture which contains the di-alkali metal salt of 2-hydroxynaphthalenecarboxylic acid and 2-hydroxynaphthalene, while keeping the mixture at a temperature of at least 80° C, then adjusting the pH-value to about 6 to 7 by means of aqueous mineral acid, separating the lower phase at at least 80° C, cooling the upper phase to about 15° to 25° C, separating the 2-hydroxynaphthalene, then adjusting the pH-value to about 1 to 2 by means of aqueous mineral acid and isolating the separated 2-hydroxynaphthalenecarboxylic acid. By this novel process, work intensive operations, expensive technical apparatuses which are suspectible to repairs, solvents which do not participate directly in the reaction and therewith complicated regenerations, as known from the present art, are completely avoided. It permits clear and very easy separation of the reaction products at only one and the same stage in the process and allows in advantageous manner continuous operation.

8 Claims, No Drawings

PROCESS FOR ISOLATING 2-HYDROXYNAPHTHALENE CARBOXYLIC ACIDS FROM REACTION MIXTURES OF THE ALKALI METAL SALTS OF 2-HYDROXYNAPHTHALENE WITH CARBON DIOXIDE

The invention relates to an improved process for isolating 2-hydroxynaphthalenecarboxylic acids from reaction mixtures of the alkali metal salts of 2-hydroxynaphthalene with carbon dioxide, which mixtures essentially consist of the alkali metal salts of 2-hydroxynaphthalenecarboxylic acids, of 2-hydroxynaphthalene and of resinous by-products of different, in most cases unknown constitution, non-saliferous impurities and free 2-hydroxynaphthalene.

In the known industrial processes, the separation of the accompanying substances is carried out in a very expensive manner by separating the 2-hydroxynaphthalene in several steps by distillation and, after neutralisation of the remaining mixture by filtration in two steps, separating the acid resinous by-products and their not-saliferous analogues in separate sedimentation and filtration processes (cf. FIAT Final Report No. 1308). It is above all the partly sticky, partly smeary consistency of the side reaction products, hereinafter referred to as "resin," which are composed of a great number of individual components and formed by oxidation and/or dehydration which puts considerable demands on apparatus and personnel to master the technical problems arising in the separation of 2-hydroxynaphthalenecarboxylic acids. Cloggings of filters and tubes, high susceptibility to repairs and therewith deficiency of capacity characterize these personnel-intensive technical processes. Owing to the importance of the 2-hydroxynaphthalenecarboxylic acids as intermediate products for a great number of dyestuffs and pigments, great efforts have since been made in order to develop more favourable alternatives of the methods for the isolation of the accompanying substances of the carboxylation. In particular, there have been proposed treatments of the reaction mixtures of alkali metal salts of 2-hydroxynaphthalene and carbon dioxide with solvents, optionally in combination with neutralization processes, in order to master the problems by way of extraction. The mentioned solvents, for example dialkyl- or diaryl ethers, diaryls and alkylnaphthalenes or mixtures thereof, are said to possess a sufficient dissolving power for 2-hydroxynaphthalene and the "resin" (cf. U.S. Pat. Nos. 2,132,356; 3,405,169; 2,132,357; German Offenlegungsschrift No. 2 132 296).

However, owing to the explosiveness of the first, the poisonousness and the low density difference to the aqueous 2-hydroxynaphthalenecarboxylic acid phase of the latter, and in particular owing to the increased expenditure of regeneration involved in the use of solvents that do not participate in the reaction and owing to insufficient dissolving power for the one or the other "resin" component, no industrial applications of these proposals have become known up to now.

Now, we have found that the disadvantages in the isolation of 2-hydroxynaphthalenecarboxylic acids from reaction mixtures of the alkali metal salts of 2-hydroxynaphthalene with carbon dioxide can be avoided by diluting with water the reaction mixture which contains the di-alkali metal salt of the 2-hydroxynaphthalenecarboxylic acid and 2-hydroxynaphthalene, while keeping the mixture at a temperature of at least 80° C, then adjusting a pH-value of about 6 to 7 by means of aqueous mineral acid, after deposition at at least 80° C separating the lower phase, cooling the lower phase to about 15° to 25° C, separating the 2-hydroxynaphthalene, subsequently adjusting the pH-value with aqueous mineral acid to about 1 to 2 and isolating the 2-hydroxynaphthalenecarboxylic acid that has separated.

2-Hydroxynaphthalene does not have the undesired properties of the other proposed solvents and is, therefore, excellently suitable for the extractive removal of the resinous accompanying substances from carboxylation mixtures of alkali metal salts of 2-hydroxynaphthalene, provided that the operations are carried out above 80° C. In this case, the 2-hydroxynaphthalene forms in the presence of water a molten liquid phase of low viscosity and has a very high dissolving power for all "resin"-constituents and, owing to the high density difference to the aqueous phase present, an excellent capacity of forming in a short time sharp phase-separating layers, whereby a static as well as dynamic phase separation, if desired even in continuous manner, becomes problemless and therewith technically feasible in very simple manner. Especially owing to the possibility of carrying out all separation operations in completely liquid phase, any subsequent washing and recycling processes are technically simply realizable, so that is possible in every case to separate the carboxylation mixture in a uniform aqueous solution of the 2-hydroxynaphthalenecarboxylic acids, which is completely freed from 2-hydroxynaphthalene and "resin," on the one hand, and a uniform, liquid organic phase consisting of the total accompanying substance from the carboxylation of the alkali metal salts of 2-hydroxynaphthalene, on the other hand. For this purpose, only automatically operating liquid/liquid or solid/liquid separating apparatuses are required. Manual work is not necessary; just controlling functions are necessary.

The desired 2-hydroxynaphthalenecarboxylic acids can be separated in very pure form from the aqueous solution of the 2-hydroxynaphthalenecarboxylic acids by acidification in known manner; the organic phase can be converted without difficulty by distillation into pure, re-usable 2-hydroxynaphthalene.

The process of the invention is carried out by mixing with water the mixture obtained after the reaction of alkali metal salt of 2-hydroxynaphthalene with carbon dioxide and adjusting a temperature of at least 80° C, in particular of from about 85° to 100° C, adjusting a pH-value of about 6 to 7 by means of a mineral acid, for example hydrochloric acid or sulfuric acid, and optionally adding such a quantity of 2-hydroxynaphthalene that at least 1 mole of 2-hydroxynaphthalene is present per mole of 2-hydroxynaphthalenecarboxylic acid. The mixing water may be used in different amounts. For the further working up, however, a ratio of about 4 to 6 parts of water per 1 part of organic product has proved particularly favourable.

The two-phase mixture obtained in such a manner and having a temperature of about 80° to 100° C separates upon shut-off of the mixing device or, in the case of continuous operation, upon introduction into a quieting zone, under very rapid formation of a sharp phase limit into a lighter aqueous layer and a specifically heavier organic layer which can be separated discontinuously or continuously by drainage, overflow or separation. A dynamic phase separation in a rotating gravity field can slso be effected with advantage, by-passing a quieting zone.

the two separated phases are not yet uniform in the sense of the above-given definition, since the aqueous layer still contains dissolved 2-hydroxynaphthalene and the organic layer still contains small amounts of dissolved 2-hydroxynaphthalenecarboxylic acids. By cooling the first to about 15° to 25° C, it is possible to quantitatively precipitate the dissolved 2-hydroxynaphthalene and separate it, with the aid of so-called "thickeners," for example decanting centrifuges or hydrocyclones, in the form of a pumpable suspension and to recycle it in the aqueous mixing stage. In corresponding manner, the treatment of the organic layer with water at about 80° to 100° C and following phase separation analogous to the first-described leads in very simple manner to a uniform organic phase liberated from 2-hydroxynaphthalenecarboxylic acids and a "washing water," which is correspondingly recycled to the aqueous mixing stage and replaces there from this time on the fresh water initially used.

With this use of two cycles, the separation of the total 2-hydroxynaphthalenecarboxylic acids as well as of the complete 2-hydroxynaphthalene/"resin" phase can both be conducted at only one and the same stage of the process, without manual work.

The acidification of the aqueous phase, for better formation of crystals preferably at about 80° C, leads in known manner to the precipitation of the 2-hydroxynaphthalenecarboxylic acids which are then isolated by filtration.

ticularly advantageous, because not only the removal of the 2-hydroxynaphthalene formed by several distillations, which is absolutely necessary in the conventional working up, would be avoided, but the favourable working up by liquid phase separation could be coupled with a decisive simplification of the caboxylation process.

The process of the invention is especially suitable for the working up of the carboxylation mixtures obtained according to the process of patent application Ser. No. 583,296, now abandoned, filed the same day in this state, corresponding to German patent applications P 24 26 850.6, dated June 4, 1974, and P 25 22 175.4, dated May 17, 1975.

In the process of the invention, work-intensive operations, expensive technical apparatuses which are susceptible to repairs, solvents which do not participate directly in the reaction and therewith complicated regenerations are completely avoided. It permits clear separation of the reaction products at only one and the same stage of the process and allows in advantageous manner continuous operation. Therefore, the process of the invention represents a considerable technical progress.

The process of the invention is illustrated hereinafter with its essential stages with the aid of a diagram which shows, by way of example, the working up of a carboxylation of the sodium salt of 2-hydroxynaphthalene in the 1.5-fold molar quantity of 2-hydroxynaphthalene as the solvent, without limiting its application to this particularly described problem. The parts mentioned are parts by weight.

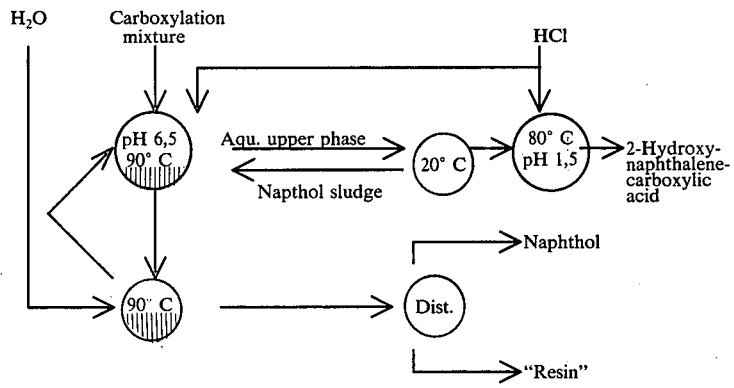

The organic phase is separated, likewise in known manner, by distillation under reduced pressure in pure re-usable 2-hydroxynaphthalene (distillate) and waste products (sump).

The process of the invention is suited for the working up of all known carboxylation mixtures of alkali metal salts of 2-hydroxynaphthalene, in particular such mixtures which on the ground of the reaction parameter contain the amount of alkali metal salts of 2-hydroxynaphthalene and/or free 2-hydroxynaphthalene which is required for a sharp separation and a sufficient dissolving power. Thus, all carboxylation products which can be obtained in 2-hydroxynaphthalene as solvent or under liberation of 2-hydroxynaphthalene are especially suitable for this working up process. To these belong, for example the "liquid carboxylation processes" of alkali metal salts of 2-hydroxynaphthalene in an excess of 2-hydroxynaphthalene described in German Pat. Nos. 423,034 and 955,598, and the conventional so-called "dry carboxylations" (FIAT Final Report No. 1308); for the latter the process of the invention is par- 3071.4 Parts of a carboxylation mixture consisting of 740.4 parts of disodium salt of 2-hydroxynaphthalene-3-carboxylic acid, 159.4 parts of sodium salt of 2-hydroxynaphthalene, 2068.4 parts of 2-hydroxynaphthalene and 95.5 parts of "resin," prepared by a 5 hours' reaction of a solution of 1273.7 parts of sodium salt of 2-hydroxynaphthalene in 1657.3 parts of 2-hydroxynaphthalene with carbon dioxide at 210° C and 50 atmospheres gauge, were mixed at 90° C with the 4-fold amount of water (dissolution), adjusted to pH 6.5 by the addition of 352.9 parts of 30% hydrochloric acid and the stirrer was switched off. The lower phase which settled down very rapidly was drained into a second container. The remaining upper phase was cooled to 20° C, whereupon the totality of 2-hydroxynaphthalene dissolved in it precipitated. Upon passage of the resulting suspension over a decanting centrifuge, a clear aqueous solution of the 2-hydroxynaphthalene-3-carboxylic acid was obtained in addition to a thickened suspension of 2-hydroxynaphthalene which was recycled to the next dissolving stage.

The lower phase that had been drained was washed by the addition of the 4-fold quantity of 90° C hot water, while stirring, and, after deposition, passed into a distillation plant, whereas the supernatant washing water was likewise recycled to the dissolving stage and used there as mixing water instead of the fresh water used in the first batch.

After having recycled several times the thickened 2-hydroxynaphthalene suspension and the washing water, a constant concentration equilibrium of all reaction components in both separation phases eventually established and per bath constant amounts of aqueous solution of the 2-hydroxynaphthalene-3-carboxylic acid on the one hand, and organic lower phase on the other hand, were obtained.

The first was heated to 80° C, adjusted to pH 1.5 by the addition of 340.7 parts of 70% sulfuric acid, the 2-hydroxynaphthalene-3-carboxylic acid that had thereby separated was filtered off, washed with water and dried at 80° C. 600 Parts of 2-hydroxy-naphthalene-3-carboxylic acid were obtained in this process stage, which corresponded to a practically quantitative isolation of the compound contained in the starting mixture.

The lower phase that had been separated was distilled under reduced pressure, whereupon a distillate consisting of 2196.7 parts of 2-hydroxynaphthalene and 251.7 parts of water was obtained, which was free from resinous impurities and could be directly used for the preparation of carboxylatable sodium salt of 2-hydroxynaphthalene. The distillation sump consisted of 37.6 parts of 2-hydroxynaphthalene and the total "resin" (95.6 parts). It could be burnt without difficulty.

When using instead of the apparatuses described continuously operating mixing, separating, filtrating, distillating and drying apparatuses, the working up which can then be carried out fully continuously, gives an identical result. The quantities mentioned are then to be understood as quantity per time unit.

We claim:

1. A process for the isolation of 2-hydroxynaphthalenecarboxylic acid from its reaction mixture derived from the reaction of the alkali metal salts of 2-hydroxynaphthalene with carbon dioxide which comprises diluting the reaction mixture with such an amount of water that the ratio of water to organic product is about 4:1 to 6:1, maintaining the reaction mixture at a temperature of about 80° to 100° C, adjusting the pH to about 6 to 7 by addition of aqueous mineral acid, adding, if required, such an amount of 2-hydroxynaphthalene that 1 mole or more of 2-hydroxynaphthalene is present per mole of 2-hydroxynaphthalenecarboxylic acid, allowing the phases to separate into an upper and lower phase, separating the lower phase at a temperature of about 80° to 100° C, cooling said upper phase to a temperature of about 15° to 25° C to precipitate 2-hydroxynaphthalene, separating the precipitate, adjusting the pH of the remaining liquid upper phase to about 1 to 2 and isolating the 2-hydroxynaphthalenecarboxylic acid that has separated.

2. A process as claimed in claim 1, wherein the 2-hydroxynaphthalene isolated from the upper phase is recycled to said rection mixture.

3. The process of claim 1, wherein 2-hydroxynaphthalene carboxylic acid is removed from the lower phase by extraction with hot water and subsequently obtaining 2-hydroxynaphthalene from the remainder of the lower phase by distillation at reduced pressure.

4. A process as claimed in claim 3, wherein the 2-hydroxynaphthalene recovered from the lower phase is recycled to said reaction mixture.

5. A process as claimed in claim 1, wherein the dialkali metal salt of the 2-hydroxynaphthalenecarboxylic acid and the 2-hydroxynaphthalene are present in the reaction mixture in a molar ratio of about 1:1 to about 1:10, preferably in a ratio of about 1:2.5.

6. A process as claimed in claim 1, wherein the reaction mixture is diluted with about the 4- to 5-fold quantity of water.

7. A process as claimed in claim 1, wherein the process is carried out in continuous operation.

8. A process as claimed in claim 3, wherein the lower phase extraction water is recycled to said reaction mixture.

* * * * *